(12) United States Patent
Atabekov et al.

(10) Patent No.: US 6,573,427 B1
(45) Date of Patent: Jun. 3, 2003

(54) RECOMBINANT CONSTRUCT FOR ENHANCEMENT OF GENE EXPRESSION IN PLANTS

(76) Inventors: Joseph Atabekov, Lomonosovski prospekt 15-142, Moscow 117311 (RU); Timo Korpela, Kasarminkatu 5 as 8, FIN-20500 Turku (FI); Yurii Dorokhov, Profsojuznaja Street 146-3-187, Moscow 117321 (RU); Sergey Morozov, Tvardovsky Street 1-228, Moscow 153458 (RU)

( * ) Notice: Subject to any disclaimer, the term of this patent is extended or adjusted under 35 U.S.C. 154(b) by 0 days.

(21) Appl. No.: 09/445,092
(22) PCT Filed: May 28, 1998
(86) PCT No.: PCT/FI98/00445
§ 371 (c)(1),
(2), (4) Date: Feb. 2, 2000
(87) PCT Pub. No.: WO98/55636
PCT Pub. Date: Dec. 10, 1998

(30) Foreign Application Priority Data

Jun. 2, 1997 (FI) .................................................. 972325

(51) Int. Cl.⁷ .......................... C12N 15/82; C07H 21/04
(52) U.S. Cl. ...................... 800/280; 435/419; 435/468; 536/23.1; 536/23.72; 800/278
(58) Field of Search ................................. 435/419, 468; 800/278, 280; 536/23.1, 24.1, 23.72

(56) References Cited

U.S. PATENT DOCUMENTS 5,217,879 A * 6/1993 Huang et al.
5,316,931 A * 5/1994 Donson et al.
5,633,441 A * 5/1997 De Greef et al.
5,633,447 A   5/1997 Ahlquist et al.

FOREIGN PATENT DOCUMENTS

| EP | 0573767 | | 12/1993 |
|---|---|---|---|
| EP | 0672754 | | 9/1995 |
| FI | 963860 | | 9/1996 |
| WO | WO-91/13994 | * | 9/1991 |
| WO | WO 93 03143 | | 2/1993 |
| WO | 9303161 | | 2/1993 |
| WO | WO 9426912 | | 11/1994 |
| WO | 9527044 | | 12/1995 |
| WO | 9534688 | | 12/1995 |
| WO | WO 96 12028 | | 4/1996 |

OTHER PUBLICATIONS

Donson et al. System expression of a bacterial gene by a tobacco mosaic viru–based vector vol. 88 pp. 7204–7208 Aug. 1991Genetics.*
Yusibov et al (1997) Proc. Natl. Acad. Sci. 94:5784–5788.*
The EMBO Journal, vol. 16, No 12, 1997, Susan M. Angell et al, p. 3675—p. 3684.
FEBS, vol. 336, Dec. 1993, Masashi Mori et al, p. 171—p. 174.

* cited by examiner

*Primary Examiner*—James Ketter
*Assistant Examiner*—Bronwen M. Loeb
(74) *Attorney, Agent, or Firm*—Birch, Stewart, Kolasch & Birch, LLP

(57) ABSTRACT

The present invention focuses on the super-expression of foreign genes in transgenic cells by combining within a single cDNA construct and respective RNA transcript, several trans- and cis-acting genetic elements of viral origin which act in concert.

9 Claims, 5 Drawing Sheets

RECOMBINANT CONSTRUCT FOR ENHANCEMENT OF GENE EXPRESSION IN PLANTS

This application is the national phase under 35 U.S.C. §371 of PCT International Application No. PCT/FI98/00445 which has an International filing date of May 28, 1998, which designated the United States of America.

This invention describes a DNA construct based on viral sequences which are capable of activating or increasing the expression of a gene in recombinant DNA-containing tissue. The invention is useful for increasing the expression of a gene, derived from heterologous plant species, or has non-plant origin. The invention will facilitate in the genetic engineering to super-express the proteins of interest or express novel plant phenotypes of economic or investigative value.

FIELD OF THE INVENTION

This invention is related to molecular biology and biotechnology exploiting plant genetic engineering by recombinant DNA technology.

BACKGROUND OF THE INVENTION

Structurally polycistronic RNAs of many plant and animal viruses belonging to so-called Sindbis-like supergroup are functionally monocistronic: only the 5'-proximal gene can be translated by eukaryotic ribosomes. All the internal translationally silent genes are expressed from subgenomic RNAs (sgRNA) produced by transcription of the minus-copy of the full-length genomic RNA from internal sites—subgenomic promoters (sgPr). All RNA viruses produce during their replicative cycle the virus-specific RNA-dependent RNA polymerase (replicase) which is essential for the synthesis of various species of viral RNA. The replicase gene is localized 5'-proximally within the monopantite genomes of the members of Sindbis-like viruses (e.g. tobacco mosaic virus, TMV, potato virus X, PVX, brome mosaic virus, BMV), i.e. represent the only translatable gene of the polycistronic genome (for a review, see Bruening et al. (1979) In "Molecular Biology of Plants", Academic Press, New York-London. pp.241–272). Specific cis-acting sequences within the minus-copy of the genomic RNA are required for synthesis of sgRNAs. The multifunctional nature of replicase allows it to recognize these internal sequences (sgPrs) to synthesize sgRNAs by partial transcription of the negative-scrand RNA. This mechanism has been clearly established for some plant viruses in vitro (Miller et al. (1985) Nature 313, 68–70) and in vivo (Gargouri et al. (1989) Virology 171, 386–393).

It has been shown that the chimeric TMV (Donson et al. (1991) Proc.Natl.Acad.Sci.USA 88, 7204–7208) and PVX (Chapman et al. 1992) Plant J. 2, 549–557; Hammond-Kosack et. al. (1995) Mol.Plant-Microbe Int. 8, 181–185) vectors could be constructed by insertion of the foreign genes downstream of a sgPr that permits the expression of introduced genes from appropriate sgRNA. This means that viral replicase can recognize the sgPr at different positions within recombinant minus-strand. Moreover, viral replicase expressed from the integrated cDNAs in transgenic plants can replicate viral RNAs and produce subgenomic RNAs (Leiser et al. (1992) Proc.Natl.Acad.Sci.USA 89, 9136–9140). Thus, it could be presumed that the replicase will be able to act in trans to recognize in vivo the specific sgPr not only in full-length viral genome but also in the short chimeric minus-sense RNA transcripts carrying a foreign gene (in antisense orientation). This could result in producing the respective sgRNA by the mechanism adapted for viral sgRNA synthesis.

Contrary to the majority of eukaryonic mRNAs several viral and cellular mRNAs are translated by alternative-internal ribosome entry mechanism that bypasses the normal cap recognition step and 5'-nontranslated sequence scanning. In particular, the genome of crucifer tobarnoviruses (crTMV) (Dorokhov et al. (1994) FEBS Letters 350, 5–8) contains two cis-acting sequences mediating internal ribosome entry and translation of the 3'-proximal genes of crTMV RNA. These elements can be used in constructing functionally dicistronic or polycistronic eukaryotic mRNAs. In this invention we found that these elements can be expoited in certain conditions for the expression at translational level of more than one reporter gene within a polycistronic mRNA in eukaryotic cells.

The complete nucleotide sequence of the PVX genome has been reported for Russian (Skryabin et al. (1988a) Nucleic Acid Res. 16, 10929–10930) and several other strains (for example, see Querci et al. (1993) J.Gen.Virol. 74, 2231–2255.). The PVX genome contains five ORFs coding for the 165 kDa replicase, three movement proteins (MPs) (25 kDa, 12 kDa and 8 kDa) and coat protein (CP) (FIG. 1). The replicase protein is translated directly from the genomic RNA, and its expression is controlled by the 5'-untranslated genomic leader sequence ($\alpha\beta$-sequence). The $\alpha\beta$-leader has been shown to enhance strongly the translation of foreign genes both in vitro (Smirnyagina et al. (1991) Biochimie 73, 587–598) and in vivo Tomashevskaya et al. (1993) J.Gen.Virol. 74, 2717–2724). The separate sgRNAs are produced in PVX infection for the MPs and CP expression which are 3'-coterminal with the genomic RNA (FIG. 1) (Morozov et al. (1991) J.Gen. Virol. 72, 2039–2043). The precise borders of the PVX sgPrs are unknown, however, it has been experimentally shown that the 81 nt sequence including 15 5'-terminal nucleotides of the PVX CP gene and 66 nt upstream sequence is active in vivo as sgPr (Chapman et al. (1992) Plant J. 2, 549–557). Recently the PVX-based vectors with this engineered 81-nt-long sgPr was used for the transient expression of the pathogene elecitor gene and plant defence genes (Rommens et al. (1995) Plant Cell 7, 249–257). Using of plant RNA viruses for the introduction and expression of non-viral foreign genes in plants has been demonstrated by the cited references above as well as by French et al. (1986) (Science 231, 1294–1297). However, all these viral vectors have been capable of autonomous replication in plant cells, thus, providing a risk for cell pathogenesis in a manner typical for wild type virus. Another disadvantage of self-replicating RNA vectors is that they are not stable for the maintenance of non-viral sequences (Donson et al. (1991) Proc.Natl.Acad.Sci.USA 88, 7204–7208).

While there are distinct needs for improving expression of foreign proteins, such as industrial enzymes, medical drugs and so on in plants, there exists several technical problems. First of all, the expression levels of protein in plants are not adequate. The present invention was aimed to overcome these drawbacks.

SUMMARY OF THE INVENTION

The present invention focuses on the super-expression of foreign genes in transgenic cells by to combining within a single cDNA construct and respective RNA transcript, several trans- and cis-acting genetic elements of viral origin which will act in concert to trigger the following functional events: a) the primary chimeric continuous RNA transcript is produced by the transformed cells from plant-expressible promoter (35S promoter) (FIG. 2); b) RNA replicase produced by direct translation of the 5'-proximal gene of a single continuous primary transcript will synthesize secondary monocistronic (FIG. 3A) (or dicistronic (FIG. 3B)) mRNA as a result of the transcription from sgPr sequence. Expression of the 5'-proximal gene of these mRNAs will be enhanced by the αβ-leader. Translation of the 5'-distal gene of dicistronic mRNA (FIG. 3B) will be promoted by internal ribosome entry site (IRES) sequence derived from crTMV tobamovirus mentioned above; c) it is probable that at least part of RNA transcripts originated from sgPr will include at their 3'-end the minus copy of RNA replicase gene and genomic promoter for plus-RNA synthesis (FIG. 3A and B). It can be expected that RNA replicase produced in transgenic cell will bind with the 3'-terminal sequence of this RNA (genomic promoter) producing upon transcription the RNA molecules carrying the plus-polarity replicase gene at the 5'-end. Translation of these mRNAs will result in production of additional replicase in transgenic plant (FIG. 4).

DETAILED DESCRIPTION OF THE INVENTION

Figure 1:
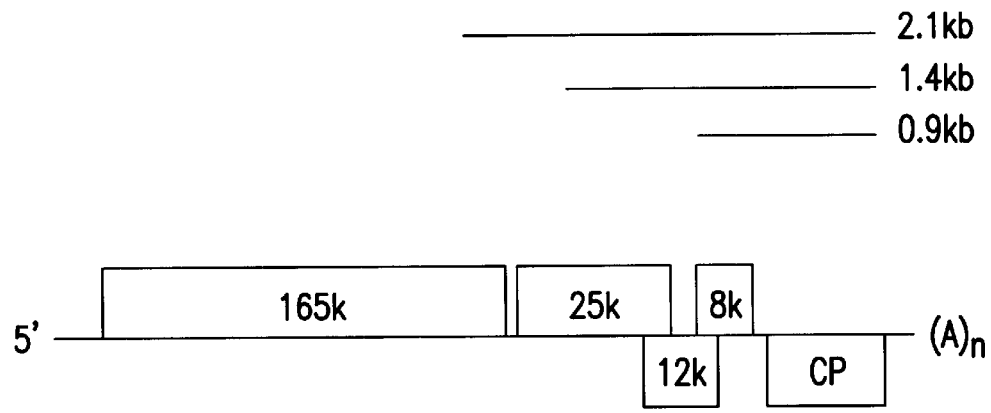
FIG. 1 Schematic representation of the PVX genome. The corresponding subgenomic RNAs art shown.

The following definitions are provided to remove ambiguities in the intent or scope of their usage. Expression refers to the transcription and translation of a gene so that a protein is synthesized. Super-expression means the expression at least several-fold higher than the expression in normal conditions. Promoter refers to the sequence at the 5' end of a structural gene which directs the initiation of DNA transcription. Promoter sequences are necessary to drive the expression of the downstream gene(s). Eukaryotic (including plant-specific) promoters generally contain the TATA box about 10–35 bp 5' to the transcription start site. 35S promoter refers to a plant-expressible cauliflower mosaic virus promoter providing the TATA box and other sequences responsible for maximum efficiency of transcription. This promoter could also serve as a transcriptional recombinant promoter for gene expression in monocotyledonous plants (Last et al., European Parent Application number: 91304205.7) and plant anaerobic regulatory element (Peacock et al., European Patent Application number: 88300852.6).

DNA segments and new strategies for increasing the expression of desired genes in plants are disclosed in this invention. The first of these expression segments represent a unique transcription module (under the control of plant-specific promoter) consisting of PVX replicase gene at the 5'-proximal position (in sense orientation) followed by sgPr of PVX (in anti-sense orientation) fused to a polylinker sequence. The second element contains additional translations enhancer of PVX (αβ-leader sequence) placed between sgPr and polylinker providing to the higher level of gene expression. The third element contains in addition to the second element an internal ribosomal entry site (IRES) to create dicistronic mRNAs capable of co-expressing the gene of interest which can be placed under the αβ-enhancer and IRES-controlled selectable marker gene, thus, significantly simplifying selection of proper transgenic plant lines. The expression activating elements described and DNA molecules containing them are useful as a method for enhanced expression of the genes in any plant tissue.

It has been proposed recently a process for production of an exogenous gene or its product in a plant cell which comprises: inserting into a genome of a plant; a) cDNA of replicase gene from RNA plant virus, and b) cDNA of a recombinant virus genomic RNA in which nucleotide moiety at and after ATG downsream from the original translation initiation codon (the first ATG counted from the 5'-end) in the cDNA of CP gene is replaced with a desired exogenous gene; or inoculating a plant cell including cDNA of replicase gene of a plant virus with RNA synthesized from the cDNA of recombinant virus genomic RNA (Mori et al., EPO Patent application No. 0573767, A1 931215). In contrast to our patent application for expression of an exogenous gene the cited application suggested to employ two cDNA constructions: cDNA of replicase gene and a recombinant virus genetic RNA where exogenous gene is present instead of natural CP gene. This approach is cumbersome and difficult to put into practice because it requires double plant cell transformation. In the present invention only one plant cell transformation is required.

Viral subgenomic promoter for the heterologous gene expression was used by Gerlach et al. (PCT WO 91/13994), who have proposed a nucleic acid sequence comprising, (a) a transcriptional promoter; (b) a heterologous gene sequence operably linked to said transcriptional promoter, and (c) a sgPr ligated to the heterologous gene sequence. The proposed cDNA construction contains heterogenous gene in antisense orientation but does not the include the viral-derived replicase gene in contrast to the present invention.

Thus, the particular advantages of the present invention over the prior art of super-expression of proteins are: 1) higher yields; 2) easier methods of the protein detection and isolation; 3) the production of proteins not only in laboratory, but also in industrial conditions.

Viral sgPrs (including those of PVX) in viral RNA genomes contain a set of consensus sequences specific for a particular virus group (see, for example, Solovyev et al. (1994) J.Gen.Virol. 75, 259–267). All known sgPrs are operating only at RNA level. Anti-sense orientation of RNA segments refers to the RNA complementary to the mRNA being translated. Chimeric sequence or construct refers to a nucleotide sequence derived from at least two heterologous parts. Production of genetically modified plant tissue expressing a protein of interest under the control of a expression activating element and an upstream plant-specific promoter combines the specific points of the present disclosure with a variety of techniques and expedients known in the art. In most instances, alternative methods exist for each stage of the overall process. The choice of the methods depends on variables such as of the vector system for the introduction and stable maintenance of the expression activating element plant-specific promoter polyadenylation signal, the plant species to be modified and the desire regeneration strategy, the RNA polymerase gene, sgPr and the particular gene of interest to be used. For instance, although the starting point for obtaining the expression activating element is exemplified in the present application by the PVX RNA replicase gene, carefully selected other replicase genes from different plant viruses may be used as well. Accordingly, subgenomic promoter sgPr of 25K protein gene (FIG. 1) of the coat protein gene might be replaced by other related promoters.

It is important to emphasize that the expression system can be exploited in very different conditions including growing of plants in the field or growing plant in climatic chamber or algae cells and other plant cells in fermentors.

One application of the invention is to localize the synthesised proteins in vacuoles, cytoplasm or intercellular space by using a proper signal peptide sequence to translocate the proteins in the desired place.

This invention could be applied for super-expression of different proteins: a) the animal RNA-binding protein to achieve nonspecific resistance to different DNA- and RNA-containing viruses; b) normal and defective plant virus-derived CP, movement protein or replicase for providing plant virus resistance; c) plant proteins such as traumatic; d) essential amino acid-rich proteins improving nutritional value of plant crops; e) medical useful proteins such as antibodies and interferon; f) enzymes such as amylases, celluloses, protease, lipases.

It should be understood also that there may be minor sequence variations within sequences utilized or disclosed in the present invention. These variations may be determined by standard techniques. As improved means are developed for the stable insertion of foreign genes in plant cells and for manipulating the modified cells, those of ordinary skill in the art will be able to select among these alternative steps to achieve a desired result. Techniques for in vitro culture and eventual regeneration into whole plants may include steps for selecting and detecting transformed plant cells (see below, EXAMPLES). Such alternative means including also electroporation, particle gun bombardment, microinjection and direct DNA transformation as well as preferred embodiment, i.e. using T-DNA containing vectors and agrobacterial-mediated transformation.

Figure 2A:
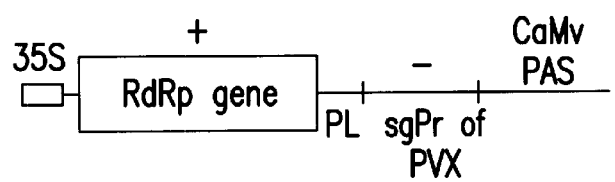
FIG. 2(A). Schematic represenation of expression activating element 1. The 35S and CaMV PAS intricate cauliflower mosaic virus 35S promoter and polyadenylation sequence, respectively. PL indicates polylinker. (+) and (-) indicate PVX-derived sequences which are identical and complementary the PVX virion RNA sequences, respectively.
Figure 2B:
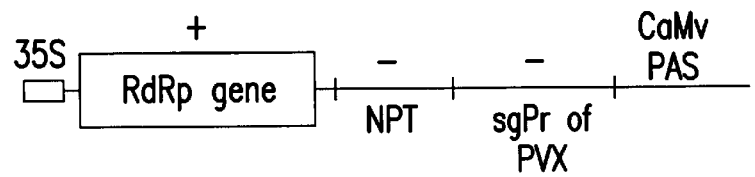
FIG. 2(B). Schematic representation of expression activating element 2. The 35S and CaMV PAS indicate cauliflower mosaic virus 35S promoter and polyadenylation sequence, respectively, (+) and (-) indicate PVX-derived sequences which are identical and complementary the PVX virion RNA sequences, respectively. NPT indicates NPTII gene.
Figure 2C:
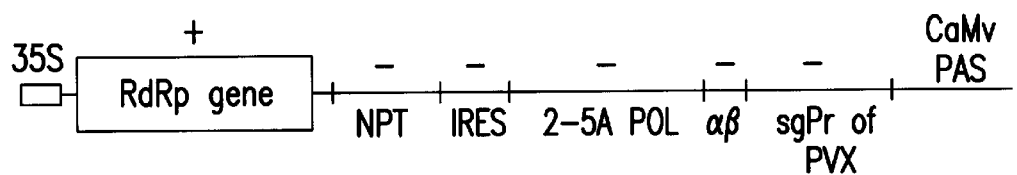
FIG. 2(C). Schematic represenation of expression activating element 3. The 35S and CaMV PAS indicate cauliflower mosaic virus 35S promoter and polyadenylation sequence, respectively, (+) and (-) indicate PVX-denived sequences which are identical and complementary the PVX virion RNA sequences, respectively, NPT indicates NPTII gene. IRES indicates internal ribosome entry site of cruciferene tobamovirus. 2–5A POL and αβ-indicate mammalian 2'–5' oligoadenylate syntethase gene and potato virus X αβ-genomic leader sequence, respectively.
Figure 2D:
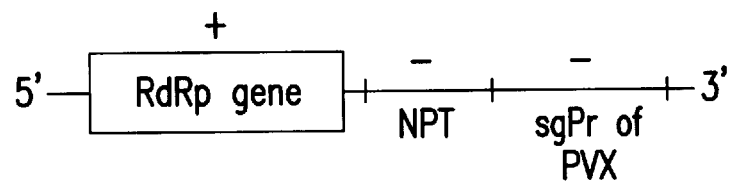
FIG. 2(D). Schematic representation of the primary transcript of expression activating element 2. Abbreviation are used as in FIG. 2(B).
Figure 2E:
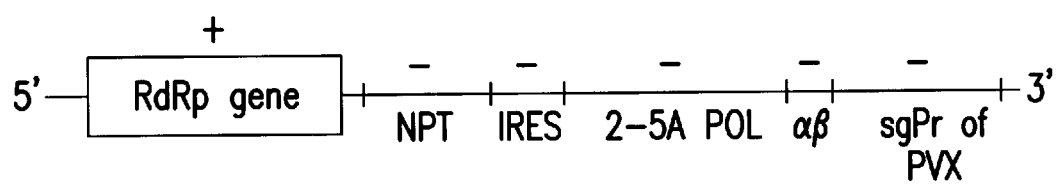
FIG. 2(E). Schematic representation of the primary transcript of expression activating element 3. Abbreviation are used as in FIG. 2(C).
Figure 3A:
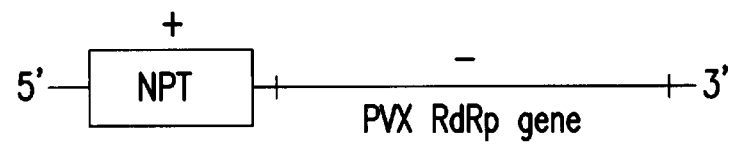
FIG. 3(A). Schematic representation of the secondary transcript of expression activating element 2. Abbreviations are used as in FIG. 2(C).
Figure 3B:
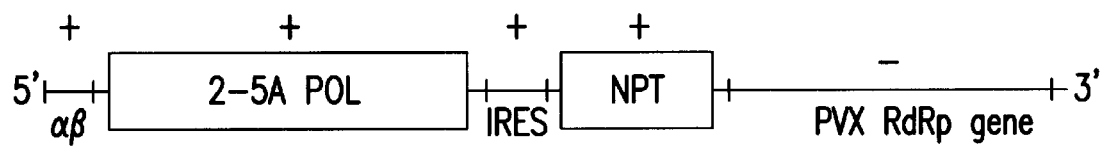
FIG. 3(B). Schematic representation of the secondary transcript of expression activating element 3. Abbreviations are used as in FIG. 2(C).
Figure 4A:
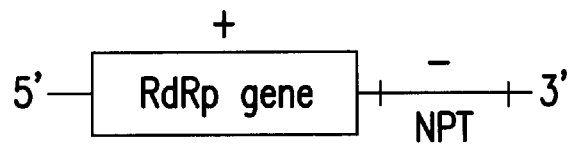
FIG. 4(A). Schematic representation of the tertiary transcript of expression activating element 2. Abbreviations are used as in FIG. 2(B).
Figure 4B:
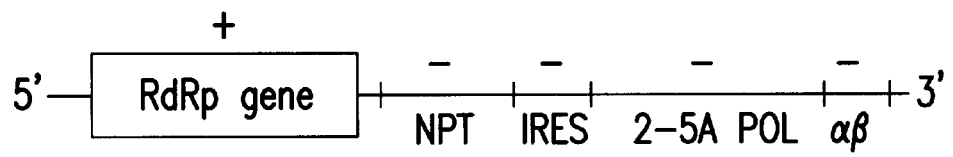
FIG. 4(B). Schematic representation of the tertiary transcript of expression activating element 3. Abbreviations are used as in FIG. 2(C).

The techniques of the present invention will significantly expand the range of plant cells into which expression activating elements can be introduced. A principal feature of the present invention in its preferred embodiment is the recombinant plasmid having an inserted plant-specific promoter and polyadenylation signal directing the transcription of viral replicase gene (in sense orientation) and heterologous gene(s) of interest (in anti-sense orientation) whose expression is directed by transcription activation from viral sgPr and by translational activation from PVX $\alpha\beta$-sequence (FIGS. 2–4). It has been determined that translational activation is the most effective when gene of interest is placed immediately 3' to the $\alpha\beta$-sequence in the respective translatable transcript (FIG. 3). To avoid significant differences in the rates of expression of genes of interest in different plant lines, the selective marker gene under the control of IRES can be inserted on the 3' side of he transcript.

The following reasoning is provided for illustrative purposes only and is not intended to limit the scope of the invention. In the transgenic plant, the single cDNA construct directs the synthesis of respective primary RNA transcript controlled by 35S promoter and polyadenylation signal (PAS) of cauliflower mosaic virus (Odell et al. (1985) Nature 313, 810–812) (FIG. 2C). The primary chimeric RNA transcript includes the PVX replicase gene at the 5' end (FIG. 2E). RNA replicase produced by direct translation of the 5'-proximal gene of a single continuous primary transcript synthesizes secondary dicistronic mRNA as a result of the transcription from sgPr sequence (FIG. 3B). Expression of the 5'-proximal gene (mammalian 2'–5' oligoadenylate synthetase gene; Truve et al. (1993) Biotechnology 11, 1048–1052) of this dicistronic mRNA will be enhanced by the $\alpha\beta$-leader (Tomashevskaya et al. (1993) J.Gen.Virol. 74, 2717–2724). Translation of the 5'-distal gene (selective marker NPTII gene) of dicistronic mRNA (FIG. 3B) will be promoted by IRES derived from crTMV tobamovirus (Dorokhov et al. (1994) FEBS Letters 350, 5–8). As a result transformed shoots expresing the secondary transcript (FIG. 3B) could be easily selected by growing on the kanamycin-containing media. The respective kanamycin-resistant plants will produce also 2'–5' oligoadenylate synthetase (FIG. 3B) conferring them the resistance to virus infection (Truve et al. (1993) Biotechnology 11, 1048–l052). It can be expected that the PVX RNA replicase produced in transgenic cell will bind with the 3'-terminal sequence of the secondary RNA (FIG. 3B) representing the PVX genomic promoter for plus-RNA synthesis producing after transcription the RNA molecules carrying the plus-polanty replicase gene at the 5'-ecd (FIG. 4). Translation of these mRNAs will result in production of additional replicase in transgenic plant.

EXAMPLES

These examples describe the cloning, plant cell electroporation, particle gun bombardment and assay strategy for studying GUS gene regulation and expression mediated by PVX sgPr and replicase.

Example 1
Construction of Plasmids Containing the PVX Replicase Gene, GUS Gene and PVX sgPr Standard molecular biological techniques were carried out according to Maniatis et al. (1982) Molecular Cloning: a Laboratory Manual. Cold Spring Harbor Laboratory, Cold Spring Harbor, N.Y. All plasmids utilized in the invention can be prepared according to the directions of the Specification by a person of ordinary skill in the art without undue experimentation employing materials readily available in the art.

The full-length PVX cDNA clone pBS118 (Morozov et al. (1990). Biochimie 72, 677–684) was used for PCR amplification of RdRp gene with PVX specific primers PVXpol5 (corresponding to the residues 1–24 of PVX genome) and PVXpol3 (corresponding to residues 4421–4451 and including artificial KpnI site at the 5' terminus). The resulting PCR fragment was cleaved by MunI and KpnI and ligated to EcoRI-KpnI-cleaved pRT 101 (Topfer et al. (1987). Nucleic Acids Res. 15, 5890), to give pRTX-Pol. The pRT101 plasmid contains plant expressible cauliflower mosaic virus 35S promoter followed by polylinker and cauliflower mosaic virus polyadenylation site. The pBS118 clone was also used for PCR-mediated amplification of PVX sgPr. The reaction was directed by the primers PVX-SGXba (corresponding to the residues 5241–5265 of PVX genome) and PVX-SGNco (complementary to the residues 5625–5651 and including artificial Nco1 site at the 5' terminus). The plasmid pTZ-G12—derivative of pTZ18R (Zelenina et al. (1992). FEBS Letters 296, 267—270) was used for PCR-amplification of β-glucuronidase (GUS) gene. The reaction was directed by universal reverse sequencing primer and the primer (24-mer) complementary to the 3' end of GUS gene and including artificial Kpn1 site. Then, the PCR products corresponding to PVX sgPr and GUS gene were cleaved with Nco1 and ligated to each other. The ligation product corresponding to the fusion of sgPr-GUS gene was isolated from agarose gel1, cleaved with Xba1 and Kpn1 and ligated to Xba1-Kpn1-cleaved pRTX-Pol, to give pRTX-PSG. This resulting clone has a following map: 35S promoter—PVX replicase gene in sense polarity—GUS gene in minus sense—PVX sgPr in minus sense.

Example 2
Protoplast Isolation and Culture

Isolation of the mesophyll protoplasts from barley leaves, was carried out according to Zelenina et al. (1992) (FEBS Lett. 296, 276–270). Protoplasts were washed in 0.375M mannitol, 10 mM MES, pH 5.8, 205 mM NaCl, 3.5 KCl, 9.4 mM $MgSO_4$, 8.4 mM $MgCl_2$, 3.4 mM $CaCl_2$, and 0.875 mM $NaHCO_3$. The protoplasts were again sedimented, washed, sedimented and resuspended in TBS9 (Tris 3.63 g/l, electrodes) and three pulses of 275V (1375 V/cm), with a pulse width of 5 ms and a delay of 100 ms, were applied betwele electrodes from a 24 μF capacitor. After allowing the protoplasts to recover for 5 seconds, the protoplast suspension was pipetted back into a mircrofuge tube to which 600 μl washing solution was added. The tubes were spun gently (<100 g) for 5 minutes, the supernatants removed and protoplasts resuspended in 1 ml of M-S culture medium. The protoplast suspension were transferred to 35 mm petri dishes which were sealed in perafilm and incubated at 25° C. in the dark to allow expression of the GUS gene.

Example 4
Assay of GUS Gene Expression in Electroporated Proproplasts

After incubation for 44 to 48 hours, 400 μl washing solution (0.3M mannitol, 156 mM NaCl, 3.5 mM KCl, 9.4 mM $MgSO_4$, 8.4 mM $MgCl_3$, 3.4 mM $CaCl_2$, 0.9 mM $NaHCO_3$, pH6.0) was added to each dish and each protoplast sample was gently pipetted into a microfuge tube. The tubes were centrifuged at 100×g for 8 minutes and supernatant was discarded. Protoplats pellets were either stored at −80° C. until required or used immediately. Each pellet was resuspended, with the aid of a vortex mixer, in 250 μl extraction buffer (Jefferson et al. (1987) Plant Molecular Biology Report 5, 387–405). The samples were sonicated on ice for 5 seconds using a Labsonic 1510 sonicator set at 55W, equipped with a microtip probe. Debris was pelleted by centrifugation in a microfuge for 1 minute and the clear supernatant was assayed for total protein using a Bio-Rad kit according to the manufacturer's recommendations. For each set of constructs the fluorometric GUS assay (Jefferson et al. (1987) Plant Molecular Biology Report 5, 387–405) was performed on an aliquot of the supernatant containing a fixed amount of total protein in the range of 5 to 50 μg dissolved in 100 μl lysis buffer. A further 100 μl extraction buffer containing 2 mM 4-methyl-umbelliferyl-3-glucuroaid (MUG) was added, the mixture was vortexed briefly and incubated at 37° C. for a fixed time in the range of 20 to 160 minutes. The reacton was stopped by the addition of 1000 μl 0.2M $Na_2CO_3$ and fluorescence at 455 nm was measured using a Perkin-Elmer Spectrofluofimeter set at an eximrion wavelength of 365 nm.

Example 5
Particle Gun Bombardment and Resting GUS Activity in Plants

Particle gun bombardment was performed using flying disk method (for example, see Daniell (1993) (Methods in Enzymology 217, 537–557) with high-pressure helium-based apparatus PDS-1000 (Bio-Rad). Briefly, for each series of shots. DNA as precipitated on tungsten particles with calcium chloride and ethanol after the addition, while vortexting, of 10 μl of plasmid DNA (at 0.5–1.5 mg/ml to 6 mg of tungsten particles suspended in 100 μl of 50% glycerol, and then tungsten particles kept in suspension in cold 95% ethanol (90 mg/ml). After sonication 5 μl of this mixture was placed immediately on each plastic flying disk and used for bombardment when the particles had dried. A detached leaf of Nicotiana benthamiana (15–30 mm size) was placed in the center of a plastic Petri dish and bombarded on a solid support at a target distance of 7 cm. Bombardment was done with a pulse of 1350 kPa helium gas in a vacuum chamber.

Inoculated leaves were sampled 24 to 72 hrs after bombardment. PVX replicase and sgPr activity was monitored by histochemical detection of GUS expression described (Jefferson et al. (1987) Plant Molecular Biology Report 5, 387–405). Samples were infiltrated in the colorimectric GUS substrate, modified (De Block and Debrouwer (1992) Plant J. 2, 261–266) to limit the diffusion of the intermediate products of the reaction: 0.115 M phosphate buffer, pH 7.0, containing 5-bromo-4-chloro-3-indolyl-β-D-glucuronide (X-Glue) 600 μg/ml; 3 mM potassium ferricyanide; 10 mM EDTA. After incubation overnight at 37° C., the leaves fixed in 70% ethanol and examined by light microscopy.

What is claimed is:

1. A nucleic acid molecule comprising 5' to 3':
    (a) a transcriptional promoter;
    (b) a viral replicase gene;
    (c) at least one polypeptide encoding nucleic acid sequence;
    (d) a subgenomic promoter sequence, which comprises a transcription initiation site, operatively linked to the polypeptide encoding nucleic acid sequence to be expressed;

such that the replicase gene, the polypeptide encoding nucleic acid sequence and the subgenomic promoter sequence are transcribed under the action of said transcriptional promoter to give a primary transcript which is transcribed under the action of the replicase expressed from said viral replicase gene and said subgenomic promoter to give a secondary transcript;

wherein the replicase gene is in an orientation which on transcription gives a primary RNA transcript encoding for said replicase gene in a positive sense orientation; and wherein the polypeptide encoding nucleic acid sequence to be expressed and the subgenomic promoter sequence are in an orientation which on transcription gives a primary RNA transcript encoding said polypeptide encoding nucleic acid and said subgenomic promoter in a negative sense orientation.

2. The nucleic acid according to claim 1, wherein the transcriptional promoter is a eukaryotic, plant specific promoter of a plant virus.

3. The nucleic acid according to claim 1, wherein the replicase gene comprises a eukaryotic, plant specific promoter of a plant virus.

4. The nucleic acid according to claim 1, wherein said subgenomic promoter is a eukaryotic, plant specific subgenomic promoter of plant viral origin which interacts with the replicase gene.

5. The nucleic acid according to claim 1, wherein the polypeptide encoding nucleic acid sequence to be expressed encodes a desired polypeptide product selected from the group consisting of: antibiotics, toxins, hormones, enzymes, microbial proteins, and animal proteins;

wherein said polypeptide product interferes with virus infection or modifies a property selected from the group consisting of:

phenotype, sterility, salt tolerance, virus susceptibility, drought tolerance, acidity, and color of a plant; or said polypeptide product produces a detectable signal.

6. The nucleic acid according to claim 1, which additionally comprises a translational enhancer located between the transcription initiation site of the subgenomic promoter and the 5' end of the polypeptide encoding nucleic acid sequence to be expressed.

7. The nucleic acid of claim 1, which additionally comprises a translational enhancer which is αβ-leader located between the transcription initiation site of the subgenomic promoter and the 5' end of the polypeptide encoding nucleic acid sequence to be expressed.

8. A plant cell transformed with the nucleic acid of claim 1.

9. A method for expressing a polypeptide encoding nucleic acid sequence in plant cells, comprising:

introducing the nucleic acid of claim 1 into said plant cells, so that said plant cells express said polypeptide.

* * * * *